United States Patent [19]

Dellaria et al.

[11] Patent Number: 5,268,379
[45] Date of Patent: Dec. 7, 1993

[54] ETHER-CONTAINING INHIBITORS OF 5-LIPOXYGENASE

[75] Inventors: Joseph F. Dellaria, Lindenhurst; Jimmie L. Moore, Gurnee; Dee W. Brooks, Libertyville, all of Ill.

[73] Assignee: Abbott Laboratories, Abbott Park, Ill.

[21] Appl. No.: 935,079

[22] Filed: Aug. 24, 1992

[51] Int. Cl.$^5$ .................... C07D 405/12; A61K 31/47
[52] U.S. Cl. ..................................... 514/312; 546/157
[58] Field of Search ................ 546/155, 157; 514/312

[56] References Cited

U.S. PATENT DOCUMENTS 4,134,148 7/1992 Crawley et al. ................. 514/312

FOREIGN PATENT DOCUMENTS 385662 9/1990 European Pat. Off. .
385679 9/1990 European Pat. Off. .
385680 9/1990 European Pat. Off. .

*Primary Examiner*—C. Warren Ivy
*Assistant Examiner*—Zinna N. Davis
*Attorney, Agent, or Firm*—Jerry F. Janssen

[57] ABSTRACT

Compounds of the structure

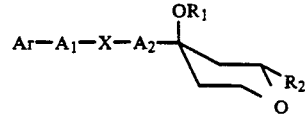

where Ar is optionally substituted carbocyclic aryl, 5- or 6-membered heterocyclic aryl, 10-membered bicyclic heterocyclic aryl containing one or two nitrogen atoms, 9- or 10-membered heterocyclic containing one or two nitrogen atoms and optionally containing a further nitrogen or oxygen atom and one oxo or thioxo substituent, benzo[b]furyl, or benzo[b]thienyl, $A_1$ is propynyl, methylene, or a direct link to X, X is oxy, thio, sulfonyl, or $NR_4$, $A_2$ is selected from

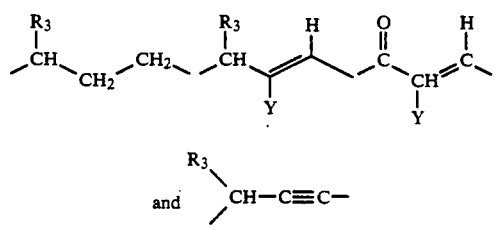

where Y is hydrogen, halogen, or nitrile; Z is hydrogen, $R_1$ is alkyl, and $R_2$ is hydrogen or alkyl are potent inhibitors of lipoxygenase enzymes and thus inhibit the biosynthesis of leukotrienes. These compounds are useful in the treatment or amelioration of allergic and inflammatory disease states.

8 Claims, No Drawings

ETHER-CONTAINING INHIBITORS OF 5-LIPOXYGENASE

TECHNICAL FIELD

This invention relates to compounds having biological activity to inhibit lipoxygenase enzymes, to pharmaceutical compositions comprising these compounds, and to a medical method of treatment. More particularly, this invention concerns certain ether-containing compounds which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxytrans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides certain triether compounds which inhibit lipoxygenase enzyme activity and are useful in the treatment of allergic and inflammatory disease states in which leukotrienes play a role.

The compounds of this invention have the structure

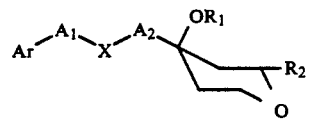

wherein Ar is selected from the group consisting of
(a) carbocyclic aryl, optionally substituted with alkyl of from one to six carbon atoms, alkoxy of from one to six carbon atoms, or halogen,
(b) 5- or 6-membered heterocyclic aryl, optionally substituted with alkyl of from one to six carbon atoms, haloalkyl of from one to six carbon atoms, alkoxy of from one to six carbon atoms, or halogen,
(c) 10-membered bicyclic heterocyclic aryl containing one or two nitrogen atoms. optionally substituted with alkyl of from one to six carbon atoms, haloalkyl of from one to six carbon atoms, alkoxy of from one to six carbon atoms, or halogen,
(d) benzo[b]furyl, optionally substituted with alkyl of from one to six carbon atoms, haloalkyl of from one to six carbon atoms, alkoxy of from one to six carbon atoms, or halogen,
(e) benzo[b]thienyl, optionally substituted with alkyl of from one to six carbon atoms, haloalkyl of from one to six carbon atoms, alkoxy of from one to six carbon atoms, or halogen,

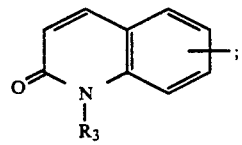
(f)

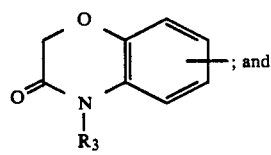
; and (g)

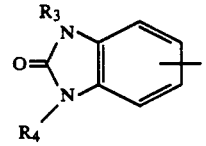
(h)

wherein $R_3$ and $R_4$ are independently hydrogen or alkyl of from one to four carbon atoms.
$A_1$ is propynyl, methylene, or a direct link to X.
X is oxy, thio, sulfonyl, or $NR_4$, wherein $R_4$ is as defined above, and $A_2$ is selected from the group consisting of

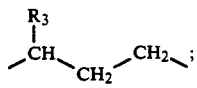
(a)

-continued

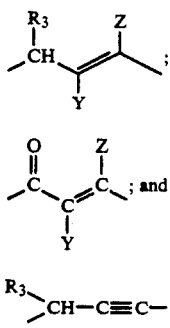

wherein R$_3$ is as defined above; Y is hydrogen, halogen, or nitrile, and Z is hydrogen or alkyl of from one to four carbon atoms, with the proviso that when X is NH, A$_2$ is

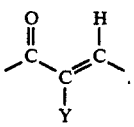

The group R$_1$ is alkyl of from one to four carbon atoms, and R$_2$ is hydrogen or alkyl of from one to four carbon atoms.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, iso- and tert-butyl, and the like.

The term "carbocyclic aryl" denotes a monovalent carbocyclic ring group derived by the removal of a single hydrogen atom from a monocyclic or bicyclic fused or non-fused ring system obeying the "4n+2π electron" or Huckel aromaticity rule. Examples of carbocyclic aryl groups include phenyl, 1-, and 2-naphthyl, biphenyl and the like.

The term "5- or 6-membered heterocyclic aryl" denotes a monovalent heterocyclic ring group derived by the removal of a single hydrogen atom from a monocyclic heterocyclic ring system obeying the "4n+2π electron" or Huckel aromaticity rule. Examples of 5, or 6-membered heterocyclic aryl groups include pyridinyl, furyl, thienyl, thiazolyl, imidazolyl, and pyrimidinyl.

The term "10-membered bicyclic heterocyclic aryl containing one or two nitrogen atoms" refers to a group selected from quinolinyl, isoquinolinyl, quinazolinyl, phthalazinyl, and quinoxalinyl.

The term "9- or 10-membered heterocyclic aryl containing one or two nitrogen and optionally containing a further heteroatom selected from nitrogen or oxygen, and one oxo or thioxo substituent" refers to a group selected from 2-oxo-1,2-dihydroquinolinyl, 2-oxo-1,2,3,4-tetrahydroquinolinyl, 3-oxo-2,3-dihydro-4H-1,4-benzoxazinyl, oxindolinyl, 3-oxo-1,2-dihydro-3H-indazolyl, 2-oxo-2,3-dihydrobenzothiazolyl, 2-oxo-2,3-dihydrobenzimidazolyl, 3-thioxo-2,3-dihydro-4H-1,4-benzoxazinyl, and 2-thioxo-1,2,3,4-tetrahydroquionlinyl.

The term "oxo" denotes a carbonyl oxygen atom.

The term "thioxo" denotes an oxo group as defined above in which the oxygen atom is replaced by a sulfur atom.

The term "propynyl" refers to a straight chain, three-carbon group containing a carbon-carbon triple bond.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

Compounds contemplated as falling within the scope of the present invention include, but are not limited to:

4-methoxy-4-[3-((napth-2-yl)methoxy)-prop-1-ynyl]tetrahydropyran;

4-methoxy-4-[3-methyl-3-(((napth-2yl)methoxy))-prop-1-ynyl]tetrahydropyran;

4-methoxy-4-[3-((napth-2yl)methoxy)-trans-prop-1-enyl]tetrahydropyran;

4-methoxy-4-[3-methyl-3-((napth-2yl)methoxy)-trans-prop-1-enyl]tetrahydropyran;

4-methoxy-4-[3-((napth-2yl)methoxy)propyl]tetrahydropyran;

4-methoxy-4-[3-((1,2-dihydro-1-methyl-2-oxoquinolin-6-yl)methoxy)-trans-prop-1-enyl]tetrahydropyran;

4-methoxy-4-[3-((1,2-dihydro-1-methyl-2-oxoquinolin-6-yl)methoxy)-trans-prop-1-enyl]-2-methyltetrahydropyran;

4-methoxy-4-[3-((4-phenylphen-1-yl)methoxy)-trans-prop-1-enyl]tetrahydropyran;

4-methoxy-4-[3-(napth-2-ylthioxy)-trans-prop-1-enyl]-tetrahydropyran;

3-(4-methoxytetrahydropyran-4-yl)-N-((napth-2-yl)methyl)-trans-propionyl amide;

3-(4-methoxytetrahydropyran-4-yl)-N-((1,2-dihydro-1-methyl-2-oxoquinolin-6-yl)methyl)-trans-propionyl amide; and 4-methoxy-4-[3-((2-(pyrid-2-yl)ethynyl)methoxy)-trans-prop-1-enyl]tetrahydropyran.

Preferred compounds are those in which Ar is selected from the group consisting of

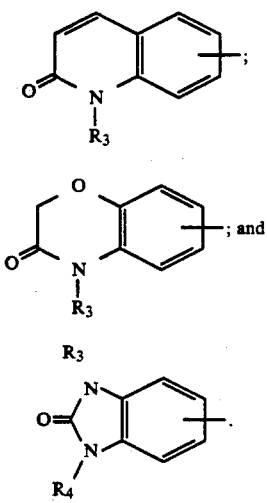

Particularly preferred compounds of the present invention are:

4-methoxy-4-[3-((1,2-dihydro-1-methyl-2-oxoquinolin-6-yl)methoxy)-trans-prop-1-enyl]tetrahydropyran; and 3-(4-methoxytetrahydropyran-4-yl)-N-((1,2-dihydro-1-methyl-2-oxoquinolin-6-yl)methyl)-trans-propionyl amide.

Lipoxygenase Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min at 37° C. followed by calcium ionophore A23187 challenge (final concentration of 8.3 μM) and the reaction terminated after 30 min by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis as illustrated in Table 1.

TABLE 1

In Vitro Inhibitory Potencies of Compounds of this Invention Against 5-Lipoxygenase from Stimulated $LTB_4$ Formation in Human Whole Blood

| Example | $IC_{50}(10^{-6}M)$ |
| --- | --- |
| 1 | 3.8 |
| 2 | 95% at 12.5 μM |
| 3 | 0.70 |
| 4 | 99% at 12.5 μM |
| 5 | 1.5 |
| 6 | 51% at 0.39 μM |
| 8 | 11% at 12.5 μM |
| 19 | 34% at 0.10 μM |
| 20 | 0.26 |
| 21 | 50% at 0.39 μM |
| 22 | 18% at 12.5 μM |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Method to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of the Compounds of this Invention

In general, the compounds of this invention are synthesized by reaction schemes I-IV as illustrated below. It should be understood that Ar, R, $R_1$ and $R_2$ as used herein correspond to the groups identified by formula I.

Scheme I

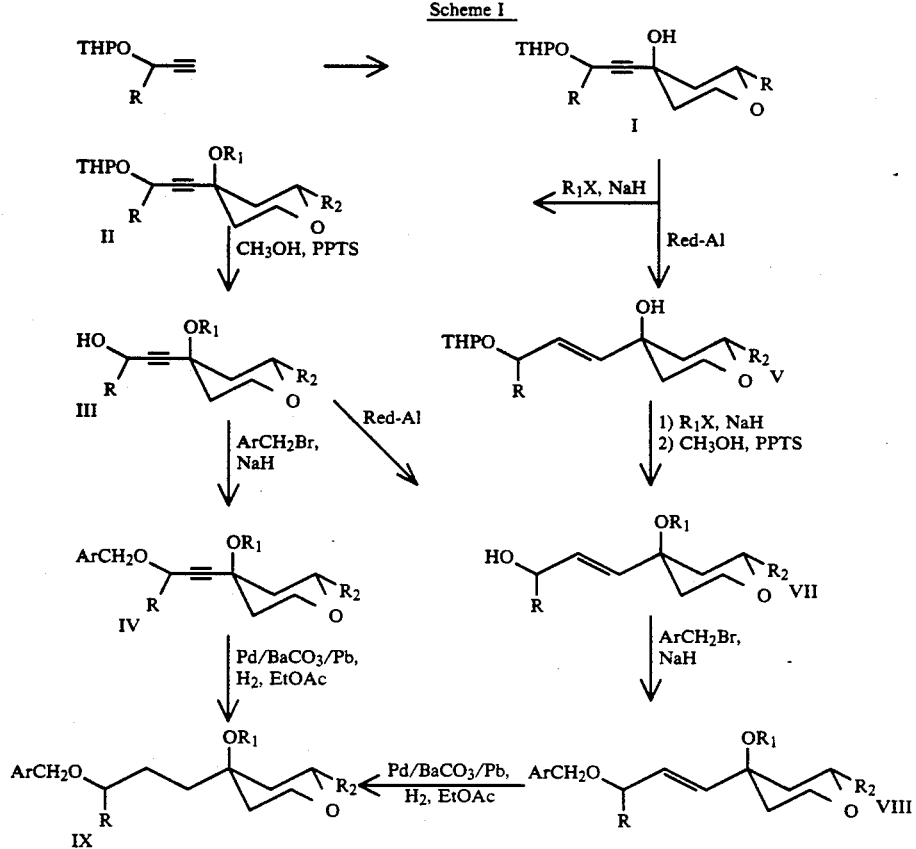

According to the foregoing reaction Scheme I, the magnesium salt of O-THP propargyl alcohol is condensed with the suitably substituted tetrahydropyran-4-one to give tertiary alcohol I. The alkynyl compound IV is prepared by alkylation of alcohol I by treatment with base, preferably sodium hydride and the desired alkyl halide. The THP protecting group is then removed, preferably by pyridinium p-toluenesulfonate in methanol, and the resulting alcohol III is alkylated by treatment with base, preferably sodium hydride and the desired arylmethyl bromide to give IV.

The alkenyl compound VIII is prepared by reduction of alkyne I to the trans olefin V with a suitable reducing agent, preferably Red-Al (sodium bis(2-methoxyethoxy)aluminum). V is then converted to VII by alkylation, deprotection, and alkylation as described for the preparation of IV. Most preferably, the alkenyl compound VIII is prepared by reduction of acetylene III to the trans-olefin VII with Red-Al; subsequent alkylation, as described above, provides VIII.

Hydrogenation of either IV or VIII, preferably cayalyzed with palladium on barium carbonate poisoned with lead gives saturated compound IX.

Scheme II

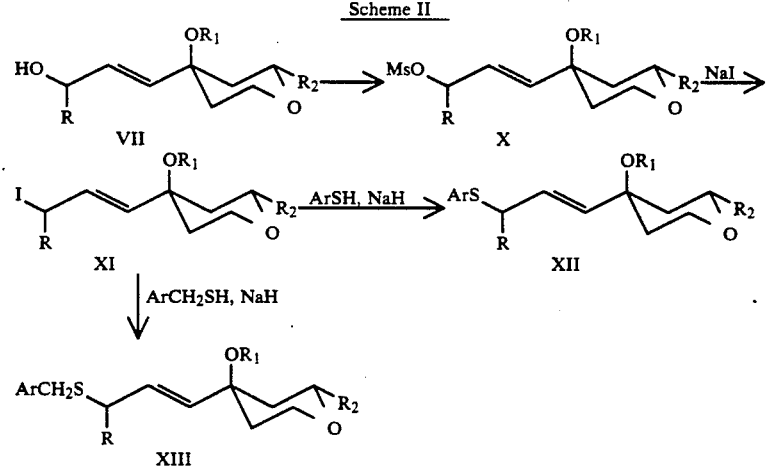

According to the foregoing reaction Scheme II, the hydroxyl group in alcohol VII is converted to suitable leaving group, preferably the mesylate. The mesylate is then converted to the iodide XI, preferably by treatment with sodium iodide. The iodide is then displaced with the desired aryl thiolate, prepared by treatment of the corresponding aryl thiol with base, preferably sodium hydride. Arylmethyl compound XIII is prepared according to the method of compound XII, except arylmethyl thiol is substituted for aryl thiol.

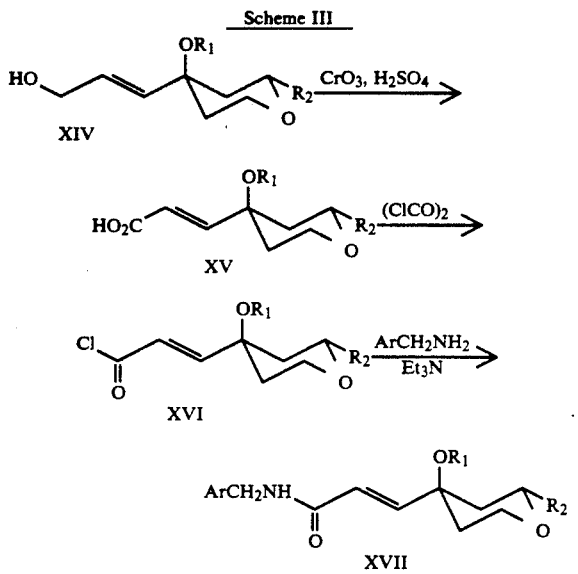

According to the foregoing reaction Scheme III, primary alcohol XIV is oxidized to carboxylic acid XV by treatment with a suitable oxidizing agent, preferably Jones Reagent. The carboxylic acid is converted to the acid chloride XVI, preferably by treatment with oxalyl chloride. Amide XVII is prepared by treatment of the acid chloride with the desired arymethylamine in the presence of a suitable base, preferably triethylamine.

alkylated by treatment with base, preferably sodium hydride and the desired alkyl halide to give XIX. Aldehyde XX is prepared by treatment of XIX with ozone and decomposition of the resulting ozonide, preferably with dimethyl sulfide. Trans olefin XXI is prepared by treatment of aldehyde XX with the ylide resulting from treatment of triethyl phosphonofluoroacetate with base, preferably tert-butyllithium. XXI is converted to acid chloride XXII by saponification with lithium hydroxide and treatment with oxalyl chloride, or to alcohol XXIII by reduction with a suitable reducing agent, preferably sodium borohydride in the presence of cerium (III) chloride.

The foregoing may be better understood from the following Examples, which are presented for the purpose of illustration and not intended to limit the scope of the inventive concept.

EXAMPLE 1

Preparation of 4-methoxy-4-[3-((napth-2-yl)methoxy)-prop-1-ynyl]tetrahydropyran

Step 1: 4-hydroxy-4-[3-(tetrahydropyran-2-yloxy)-prop-1-ynyl]tetrahydropyran

Tetrahydro-2-(2-propynyloxy)-2H-pyran (21 g, 150 mmol) was converted to the corresponding magnesium anion by deprotonation with ethyl magnesium bromide (75 mL of a 2M solution, 150 mmol) according to the method described in Org. Synth., 60: 81-7 (1981). The resulting anion was cooled to −20° C. and tetrahydro4H-pyran-4-one (14.8 g, 148 mmol) in dry THF (30 mL) was added dropwise and the resulting solution stirred for three hours. The reaction was quenched by addition of crushed ice and saturated aqueous ammonium chloride. The resulting two-layered mixture was extracted with ether (3×150 mL). The combined organic layers were dried (MgSO₄), filtered, and concentrated in vacuo. Purification by chromatography on

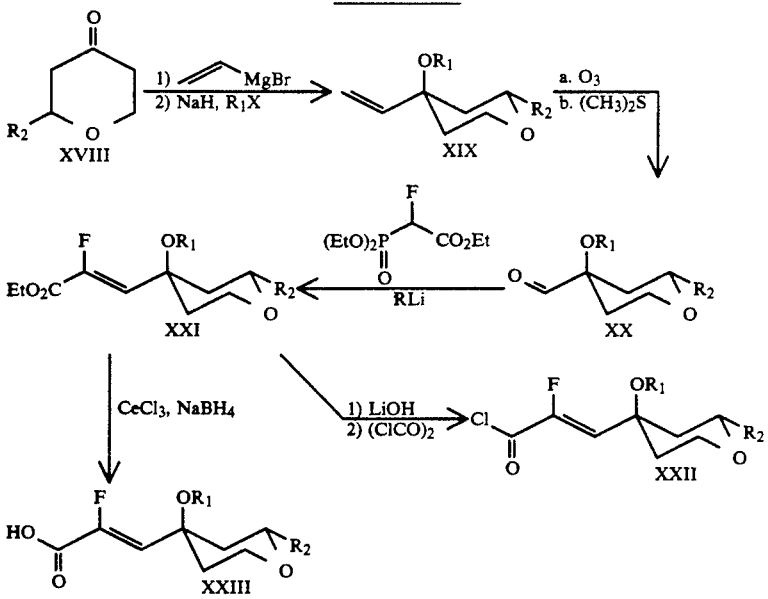

According to the foregoing reaction Scheme IV, the requisite tetrahydro-4H-pyran-4-one is treated with vinylmagnesium bromide and the resulting alcohol is silica gel (200 g, 20% ethyl acetate: hexanes) provided the desired acetylene tertiary alcohol (31.4 g, 88%).

Step 2:
4-methoxy-4-[3-(tetrahydropyran-2-yloxy)-prop-1-ynyl]tetrahydropyran To a suspension of sodium hydride (1.2 g of an 80% oil dispersion, 50 mmol) in dry THF (45 mL) was added a solution of 4-hydroxy-4-[3-(tetrahydropyran-2-yloxy)-prop-1-ynyl]tetrahydropyran (3.71 g, 15.3 mmol), prepared as in step 1. After hydrogen evolution ceased, methyl iodide (3.0 mL, 48.2 mmol) was added neat and the resulting solution was stirred overnight at ambient temperature. The reaction was quenched by addition of crushed ice and saturated aqueous ammonium chloride. The resulting two-phase mixture was extracted with ether (3×100 mL). The combined organic layers were dried ($MgSO_4$), filtered, and concentrated in vacuo. Purification by chromatography on silica gel (100 g, 10% ethyl acetate: hexanes) provided the methyl ether (3.74 g, 95%) as a colorless oil.

Step 3:
4-methoxy-4-(3-hydroxyprop-1-ynyl)tetrahydropyran

To a solution of 4-methoxy-4-[3-(tetrahydropyran-2-yloxy)-prop-1-ynyl]tetrahydropyran (3.8 g, 14.8 mmol), prepared as in step 2, in methanol (50 mL), was added a catalytic amount of pyridinium p-toluenesulfonate (PPTS). The resulting yellow solution was stirred under nitrogen for 17 hours at ambient temperature. The volatiles were removed in vacuo and the residue was dissolved in ethyl acetate and treated with saturated aqueous ammonium chloride. The organic layer was dried ($MgSO_4$), filtered, and concentrated in vacuo. Purification by chromatography on silica gel (100 g, 30% ethyl acetate: hexanes) provided the primary alcohol (1.2 g, 47%) as a colorless oil.

Step 4:
4-methoxy-4-[3-((napth-2-yl)methoxy)-prop-1-ynyl]tetrahydropyran 4-methoxy-4-(3-hydroxyprop-1-ynyl)tetrahydropyran (1.2 g, 6.97 mmol) was treated with sodium hydride in THF (18 mL). After gas evolution ceased, a solution of 2-(bromomethyl)napthalene (1.70 g, 7.67 mmol) in dry DMF (9 mL) was added. After 3 hours at ambient temperature the reaction was quenched with saturated aqueous ammonium chloride. The resulting two-phase mixture was extracted with ether (3×100 mL). The combined organic layers were dried ($MgSO_4$), filtered, and concentrated in vacuo. Purification by chromatography on silica gel (100 g, 10% ethyl acetate: hexanes) provided the title compound. (2.00 g, 92%) as a colorless oil. $^1$H NMR (300 MHz, $CDCl_3$); 7.80–7.90 (4H, m), 7.47–7.52 (3H, m), 4.70 (2H, s), 4.32 (2H, s), 3.87 (2H, dd, J=12,4.5 Hz), 3.67 (2H, dd, J=12,3 Hz), 3.40 (3H, s), 1.95 (2H, br d, J=13 Hz), 1.49 (2H, ddd, J=13,9,4.5 Hz); MS $(M+NH_4)^+=328$. Analysis calc'd for $C_{20}H_{22}O_3$: C, 77.39; H, 7.14; Found: C, 76.10; H, 7.10.

EXAMPLE 2

Preparation of 4-methoxy-4-[3-methyl-3-(((napth-2-yl)methoxy))-prop-1-ynyl]tetrahydropyran The desired compound was prepared according to the method of Example 1 except substituting tetrahydro-2-(1-methyl-2-propynyloxy)-2H-pyran for tetrahydro-2-(2-propynyloxy)-2H-pyran. 4-methoxy-4-[3-methyl-3-(((napth-2yl)methoxy))-prop-1-ynyl]tetrahydropyran was isolated as a clear oil. $^1$H NMR (300 MHz, $CDCl_3$); 7.80–7.87 (4H, m), 7.47–7.51 (3H, m), 4.93 (1H, AB, J=12 Hz), 4.69 (1H, AB, J=12 Hz), 4.34 (1H, q, J=6.5 Hz), 3.88 (2H, dt, J=12,4.5,4.5 Hz), 3.67 (2H, ddt, J=11.5,9.5,3,3 Hz), 3.40 (3H, s), 1.95 (2H, br d, J=13.5 Hz), 1.49 (2H, ddd, J=13.5,9,4.5 Hz); MS $(M+NH_4)^+=342$. Analysis calc'd for $C_{21}H_{24}O_3$: C, 77.75; H, 7.46; Found: C, 77.50; H, 7.38.

EXAMPLE 3

Preparation of 4-methoxy-4-[3-((napth-2yl)methoxy)-trans-prop-1-enyl]tetrahydropyran

Step 1:
4-hydroxy-4-[3-(tetrahydropyran-2-yloxy)-trans-prop-1-enyl]tetrahydropyran A solution of 4-hydroxy-4-[3-(tetrahydropyran-2-yloxy)-prop-1-ynyl]tetrahydropyran (10.8 g, 44.9 mmol), prepared as in Example 1, step 1, in dry THF (100 mL) was cooled to −75° C., and Red-Al (20 mL of 3.4M solution in toluene, 68 mmol) was added under a dry argon atmosphere. The cooling bath was removed and the reaction was warmed to 0° C. and quenched by addition of crushed ice and saturated aqueous ammonium chloride. The resulting two-phase mixture was extracted with ethyl acetate (4×90 mL). The combined organic layers were dried ($MgSO_4$), filtered, and concentrated in vacuo. Purification by chromatography on silica gel (100 g, 10% ethyl acetate: hexanes) provided the trans-olefin (3.71 g, 34%) as a colorless oil.

Step 2:
4-methoxy-4-[3-((napth-2yl)methoxy)-trans-prop-1-ene]tetrahydropyran The desired compound was prepared according to the method of Example I, steps 2-4 except substituting 4-hydroxy-4-[3-(tetrahydropyran-2-yloxy)-trans-prop-1-enyl]tetrahydropyran, prepared as in step 1, for 4-hydroxy-4-[3-(tetrahydropyran-2-yloxy)-prop-1-ynyl]-tetrahydropyran. Purification by chromatography on silica gel afforded 4-methoxy-4-[3-((napth-2yl)methoxy)-trans-prop-1-ene]tetrahydropyran as a colorless oil. $^1$H NMR (300 MHz, $CDCl_3$); 7.78–7.86 (4H, m), 7.47–7.52 (3H, m), 5.77 (1H, dt, J=16,5 Hz), 5.63 (1H, dt, J=16,1 Hz), 4.70 (2H, s), 4.12 (2H, dd, J=5,1 Hz), 3.67–3.8 (4H, m), 3.15 (3H, s), 1.72–1.77 (4H, m); Analysis calc'd for $C_{20}H_{24}O_3$: C, 76.89; H, 7.74; Found: C, 76.70; H, 7.71. MS $(M+H)^+=330$, $(M+NH_4)^+=347$.

EXAMPLE 4

Preparation of 4-methoxy-4-[3-methyl-3-((napth-2yl)methoxy)-trans-prop-1-enyl]tetrahydropyran The desired compound was prepared as a colorless oil according to the method of Example 3, except substituting 4-hydroxy-4-[3-methyl-3-(tetrahydropyran-2-yloxy)-prop-1-ynyl]tetrahydropyran, prepared as in Example 2, for 4-hydroxy-4-[3-(tetrahydropyran-2-yloxy)-prop-1-ynyl]tetrahydropyran. $^1$H NMR (300 MHz, $CDCl_3$); 7.75–7.85 (4H, m), 7.43–7.5 (3H, m), 5.62 (1H, dd, J=13,6 Hz), 5.53 (1H, d, J=13 Hz), 4.02 (1H, pentet, J=6 Hz), 3.65–3.82 (4H, m), 3.17 (3H, s), 1.72–1.80 (4H, m), 1.33 (3H, d, J=6 Hz); $(M+NH_4)^+=344$. Analysis calc'd for $C_{21}H_{26}O_3$: C, 77.27; H, 8.03; Found: C, 77.00; H, 7.82.

EXAMPLE 5

Preparation of
4-methoxy-4-[3-((napth-2yl)methoxy)-prop-1-yl]tetrahydropyran 4-methoxy-4-[3-methyl-3-((napth-2yl)methoxy)-trans-prop-1-enyl]tetrahydropyran (320 mg, 1.02 mmol), prepared as in Example 3, was hydrogenated over palladium on calcium carbonate, poisoned with lead, with hydrogen (1 atm) in ethyl acetate at ambient temperature for 18 hours. After flushing the reaction solution with nitrogen, the solution was filtered through a pad of celite. The filter cake was thoroughly rinsed with ethyl acetate. The combined filtrates were concentrated in vacuo and chromatographed on silica gel (14 g, 15% ethyl acetate:hexanes) to provide the title compound (214 mg, 66%) as a colorless oil. $^1$H NMR (300 MHz, CDCl$_3$); 7.75–7.87 (4H, m), 7.43–7.53 (3H, m), 4.67 (2H, s), 3.68 (4H, d,d, J=8,3 Hz), 3.52 (2H, t, J=6 Hz), 3.17 (3H, s), 1.49–1.78 (8H, m); MS $(M+H)^+ = 315$, $(M+NH_4)^+ = 332$. Analysis calc'd for $C_{20}H_{26}O_3$: C, 76.40; H, 8.33; Found: C, 76.30; H, 8.12.

EXAMPLE 6

Preparation of
4-methoxy-4-[3-((1,2-dihydro-1-methyl-2-oxoquinolin-6-yl)methoxy)-trans-prop-1-enyl]tetrahydropyran The desired compound was prepared according to the method of Example 1, step 4, except substituting 4-methoxy-4-(3-hydroxy-trans-prop-1-enyl)tetrahydropyran, prepared as in Example 3, for 4-methoxy-4-(3-hydroxyprop-1-ynyl)tetrahydropyran, and substituting 1,2-dihydro-1-methyl-2-oxo-6-(bromomethyl)quinoline for 2-(bromomethyl)naphthalene. $^1$H NMR (300 MHz, CDCl$_3$); 7.67 (1H, d, J=9 Hz), 7.52–7.58 (2H, m), 7.35 (1H, d, J=9 Hz), 6.72 (1H, d, J=9 Hz), 5.75 (1H, dt, J=15.5,8 Hz), 5.63 (1H, br d, J=16 Hz), 4.60 (2H, s), 4.10 (2H, dd, J=8,1 Hz), 3.67–3.8 (4H, m), 3.15 (3H, s), 1.72–1.77 (4H, m); MS $(M+H)^+ = 344$. Analysis calc'd for $C_{20}H_{25}NO_4$: C, 69.95; H, 7.34; N, 4.08; Found: C, 69.68; H, 7.16; N, 3.99

EXAMPLE 7

Preparation of
4-methoxy-4-[3-((1,2-dihydro-1-methyl-2-oxoquinolin-6-yl)methoxy)-trans-prop-1-enyl]-2-methyltetrahydropyran Step 1:
4-hydroxy-4-[3-(tetrahydropyran-2-yloxy)-prop-1-ynyl]tetrahydropyran The desired compound was prepared according to the method of Example 1, step 1 except substituting 2-methyltetrahydro-4H-pyran-4-one for tetrahydro-4H-pyran-4-one.

Step 2:
4-hydroxy-4-[3-(tetrahydropyran-2-yloxy)-trans-prop-1-enyl]-2-methyltetrahydropyran The desired compound was prepared according to the method of Example 3, step 1, except substituting 4-hydroxy-4-[3-tetrahydropyran-2-yloxy)-prop-1-ynyl]-2-methyltetrahydropyran, prepared as in step 1, for 4-hydroxy-4-[3-(tetrahydropyran-2-yloxy)-prop-1-ynyl]tetrahydropyran.

Step 3.
4-methoxy-4-(3-hydroxy-trans-prop-1-enyl)-2-methyl-tetrahydropyran

The desired compound was prepared according to the method of Example 1, steps 2 and 3 except substituting 4-hydroxy-4-[3-(tetrahydropyran-2-yloxy)-trans-prop-1-enyl]-2-methyltetrahydropyran for 4-hydroxy-4-[3-(tetrahydropyran-2-yloxy)-prop-1-ynyl]tetrahydropyran.

Step 4.
4-methoxy-4-[3-((1,2-dihydro-1-methyl-2-oxoquinolin-6-yl)methoxy)-trans-prop-1-enyl]-2-methyltetrahydropyran The desired compound was prepared according to the method of Example 6, except substituting 4-methoxy-4-(3-hydroxy-trans-prop-1-enyl)-2-methyltetrahydropyran for 4-methoxy-4-(3-hydroxy-trans-prop-1-enyl)tetrahydropyran.

EXAMPLE 8

Preparation of
4-methoxy-4-[3-((4-phenylphen-1-yl)methoxy)-trans-prop-1-enyl]tetrahydropyran The desired compound was prepared according to the method of Example 3, except substituting 4-pheynylphen-1-ylmethyl bromide for napth-2-ylmethyl bromide. Purification by chromatography on silica gel (16 g, 10% ethyl acetate:hexanes), provided 4-methoxy-4-[3-((4-phenylphen-1-yl)methoxy)-trans-prop-1-enyl]tetrahydropyran. (251 mg, 74%) as a colorless oil. $^1$H NMR (300 MHz, CDCl$_3$); 7.57–7.65 (4H, m), 7.32–7.52 (5H, m), 5.78 (1H, dt, J=15.5, 5,5 Hz), 5.65 (1H, d, J=15.5 Hz), 4.60 (2H, s), 3.68–3.82 (4H, m), 3.18 (3H, s), 1.72–1.80 (4H, m); MS $(M+NH_4)^+ = 356$. Analysis calc'd for $C_{22}H_{26}O_3$: C, 78.07; H, 7.74; Found: C, XXX; H, XXX.

The compounds represented in Table 2 are prepared by alkylation of the appropriate allylic alcohol, obtained as described in Examples 3 or 7 with the requisite arylmethyl or heteroarylmethyl halide according to the method of Example 1, step 4.

TABLE 2

Novel Aryl- and Heteroarylmethyloxy Substituted Olefin Triethers

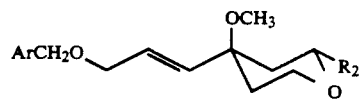

| Example | R$_2$ | Ar |
|---|---|---|
| 9 | H | -quionoxalin-6-yl |
| 10 | CH$_3$ | -quionoxalin-6-yl |
| 11 | H | -quionolin-6-yl |
| 12 | CH$_3$ | -quionolin-6-yl |
| 13 | H | 1-methyl-2-oxo-1,2,3,4-tetrahydroquinolin-6-yl |
| 14 | CH$_3$ | 1-methyl-2-oxo-1,2,3,4-tetrahydroquinolin-6-yl |
| 15 | H | 2,2,4-trimethyl-3-oxo-2,3-dihydro-4H-1,4-benzoxazin-7-yl |
| 16 | CH$_3$ | 2,2,4-trimethyl-3-oxo-2,3-dihydro-4H-1,4-benzoxazin-7-yl |
| 17 | H | 1,3-dimethyl-2-oxo-2,3-dihydrobenz-imidazol-5-yl |
| 18 | CH$_3$ | 1,3-dimethyl-2-oxo-2,3-dihydrobenz-imidazol-5-yl |

EXAMPLE 19

Preparation of 4-methoxy-4-[3-(napth-2-ylthioxy)-trans-prop-1-enyl]-tetrahydropyran

Step 1.
4-methoxy-4-(3-methanesulfonyl-trans-prop-1-enyl)tetrahydropyran 4-methoxy-4-(3-hydroxy-trans-prop-1-enyl)tetrahydropyran, prepared as in Example 3, was converted to the corresponding mesylate according to the method of Crossland and Servis, J. Org. Chem., 35, 3195–3196 (1970).

Step 2. Preparation of 4-methoxy-4-(3-iodo-trans-prop-1-enyl)tetrahydropyran To a 0° C. solution in acetone of 4-methoxy-4-(3-methanesulfonyl-trans-prop-1-enyl)tetrahydropyran (505 mg, 2.02 mmol), prepared as in step 1 was added sodium iodide (605 mg, 4.03 mmol), and the reaction was stirred for 15 min. The reaction was partitioned between ethyl acetate and brine. The organic layer was washed (2×, brine), dried (MgSO$_4$), filtered and concentrated in vacuo to provide the desired iodide (550 mg, 97%) as a dark yellow oil. The iodide was of sufficient purity to use without further purification.

Step 3.
4-methoxy-4-[3-(napth-2-ylthioxy)-trans-prop-1-enyl]-tetrahydropyran To a stirred solution of sodium hydride (186 mg, 60% dispersion in mineral oil, 4.66 mmol) in dry DMF (2 mL) was added napthyl-2-thiol (374 mg, 2.33 mmol) in dry DMF (4 mL). After gas evolution ceased, the iodide from step 2 (990 mg, 3.50 mmol), was added in dry DMF (6 mL) and the resulting mixture was stirred 0.5 hours at ambient temperature. The reaction was quenched by careful addition of saturated aqueous ammonium chloride and partitioned between ethyl acetate and brine. The organic layer was washed (1×, water; 2×, brine), dried (MgSO$_4$), filtered, and concentrated in vacuo. Purification by chromatography on silica gel (12 g, 10% ethyl acetate:hexanes) afforded the title compound (606 mg, 83%) as a yellow oil. $^1$H NMR (300 MHz, CDCl$_3$); 7.71–7.80 (4H, m), 7.40–7.50 (3H, m), 5.65 (1H,dt, J=15.5,7,7 Hz), 5.38 (1H, dt, J=15.5,1,1 Hz), 3.67 (2H, dd, J=7.5,1 Hz), 3.50–3.70 (4H, m), 2.88 (3H, s), 1.55–1.63 (4H, m); MS (M+H)+ =288. Analysis calc'd for C$_{19}$H$_{22}$O$_2$S: C, 72.58; H, 7.05. Found: C, 72.30; H, 6.85.

EXAMPLE 20

Preparation of 3-(4-methoxytetrahydropyran-4-yl)-N-((napth-2-yl)methyl)-trans-propionyl amide

Step 1.
3-(4-methoxytetrahydropyran-4-yl)-trans-propenoic acid 4-(3-hydroxy-trans-prop-1-enyl)-4-methoxy-tetrahydropyran (175 mg, 1.02 mmol), prepared as in Example 1, steps 1–3, was oxidized to the corresponding carboxylic acid by treatment with a slight excess of Jones reagent in cold acetone.

Step 2.
3-(4-methoxytetrahydropyran-4-yl)-trans-propenoyl chloride

The acid chloride was prepared by treatment of 3-(4-methoxytetrahydropyran-4-yl)-trans-propenoic acid (160 mg, 0.86 mmol), prepared as in step 1, with oxalyl chloride.

Step 3.
3-(4-methoxytetrahydropyran-4-yl)-N-((napth-2-yl)methyl)-trans-propionyl amide A solution of 3-(4-methoxytetrahydropyran-4-yl)-trans-propenoyl chloride, 2-aminomethylnapthalene (141 mg, 0.90 mmol), and triethylamine (202 mg, 2.0 mmol) in dichloromethane (4 mL) was stirred at ambient temperature for one hour. The reaction mixture was partitioned between ethyl acetate and brine. The combined organic layers were dried (MgSO$_4$), filtered, and concentrated in vacuo. Purification by chromatography on silica gel (16 g, 25% ethyl acetate:hexanes), provided the title compound (73 mg, 26%) as a colorless oil. $^1$H NMR (300 MHz, CDCl$_3$); 7.67–7.87 (4H, m), 7.52–7.58 (2H, m), 7.32–7.51 (3H, m), 6.81 (1H, d, J=15 Hz), 5.92 (1H, d, J=15 Hz), 5.87 (1H, br m), 4.70 (2H, d, J=6 Hz), 3.70–3.77 (4H, m), 3.18 (3H, s), 1.72–1.80 (4H, m); MS (M+H)+ =326,(M+NH$_4$)+ =343. Analysis calc'd for C$_{20}$H$_{23}$NO$_3$: C, 73.82; H, 7.12; N, 4.30; Found: C, 73.70; H, 7.05; N, 4.20.

EXAMPLE 21

Preparation of 3-(4-methoxytetrahydropyran-4-yl)-N-((1,2-dihydro-1-methyl-2-oxoquinolin-6-yl)methyl)-trans-propionyl amide

Step 1.
(1,2-dihydro-1-methyl-2-oxoquinolin-6-yl)methylamine

To a solution of 1,2-dihydro-1-methyl-2-oxo-6-(bromomethyl)quinoline (505 mg, 2.0 mmol) in dry THF (6 mL) was added in a dropwise fashion a solution of sodium azide (310 mg, 4.77 mmol) in 1:1 ethanol:water (7 mL). The resulting solution was stirred for 4 hours and concentrated to ~½ of the original volume. The aqueous phase was extracted with ethyl acetate (4×). The combined organic layers were dried (MgSO$_4$), filtered, and concentrated in vacuo to give the desired azide of sufficient purity to carry on without further purification. The azide (428 mg, 2.00 mmol) was reduced to the corresponding amine by exposure to propanedithiol (0.60 mL, 6.0 mmol) and triethylamine (0.84 mL, 6.0 mmol) in absolute ethanol (3 mL) and dry THF (4 mL) for seventeen hours at ambient temperature. The reaction was filtered and the filter cake washed with THF and ethyl acetate. The combined filtrates were dried (MgSO$_4$), filtered, and concentrated in vacuo to give the desired amine. Purification by silica gel chromatography (8 g, 50% ethyl acetate:hexanes, then ethyl acetate, and then 70:20:10 ethyl acetate:ethanol:THF) provided (1,2-dihydro-1-methyl-2-oxoquinolin-6-yl)methylamine.

Step 2.
3-(4-methoxytetrahydropyran-4-yl)-N-((1,2-dihydro-1-methyl-2-oxoquinolin-6-yl)methyl)-trans-propionyl amide A solution of 3-(4-methoxytetrahydropyran-4-yl)-trans-propenoyl chloride (1.0 mmol) prepared according to the method of Example 20, steps 1 and 2, (1,2-dihydro-1-methyl-2-oxoquinolin-6-yl)methylamine (188 mg, 1.00 mmol), and triethylamine (303 mg, 3.0 mmol) in dichloromethane (5 mL) was stirred at ambient temperature for one hour. The reaction mixture was partitioned between ethyl acetate and brine. The combined organic layers were dried (MgSO$_4$), filtered, and concentrated in vacuo. Purification by chromatography on silica gel (16 g, 25% ethyl acetate:hexanes, then 40% ethyl acetate:hexanes), provided the title compound (1.58 g, 44%) as a colorless solid. mp 141°-143° C.; $^1$H NMR (300 MHz, CDCl$_3$); 7.61 (1H, d, J=9 Hz), 7.47-7.55 (2H, m), 7.31 (1H, d, J=9 Hz), 6.81 (1H, d, J=15.5 Hz), 6.67 (1H, d, J=9 Hz), 6.13 (1H, br t, J=6 Hz), 5.95 (1H, d, J=15.5 Hz), 5.87 (1H, br m), 4.59 (2H, d, J=6 Hz), 3.70-3.77 (4H, m), 3.68 (3H, s), 3.18 (3H, s), 1.72-1.80 (4H, m); MS (M+H)$^+$=357, (M+NH$_4$)$^+$=374. Analysis calc'd for C$_{20}$H$_{24}$N$_2$O$_4$: C, 67.40; H, 6.79; N, 7.86; Found: C, 67.13; H, 6.62; N, 7.71.

EXAMPLE 22

Preparation of 4-methoxy-4-[3-((2-(pyrid-2-yl)ethynyl)methoxy)-trans-propen-1-yl]tetrahydropyran Step 1.
4-methoxy-4-(3-methanesulfonyl-trans-prop-1-enyl)tetrahydropyran 4-methoxy-4-(3-hydroxy-trans-prop-1-enyl)tetrahydropyran (172 mg, 1.0 mmol), prepared as in Example 3, was converted to the desired compound according to the method of Example 19, step 1.

Step 2.
4-methoxy-4-[3-((2-(pyrid-2-yl)alkynyl)methoxy)-trans-propene-1-yl]tetrahydropyran To a stirred solution of sodium hydride (45 mg, 80% dispersion in mineral oil, 1.5 mmol) in dry THF (2 mL) was added 3-(pyrid-2-yl)prop-2-ynol (133 mg, 1.00 mmol) in dry THF (1 mL). After gas evolution ceased, the mesylate from step 1 was added in dry THF (1 mL) and the resulting mixture was stirred 17 hours at ambient temperature. The reaction was quenched by careful addition of water and partitioned between ethyl acetate and brine. The organic layer was dried (MgSO$_4$), filtered, and concentrated in vacuo. Purification by chromatography on silica gel (12 g, 25% ethyl acetate:hexanes), provided the desired compound (70 mg, 24%) as a colorless oil. $^1$H NMR (300 MHz, CDCl$_3$); 8.58 (1H, br d, J=4.5 Hz), 7.67 (1H, dt, J=2,8,8 Hz), 7.46 (1H, d, J=8 Hz), ca 7.25 (1H, m), 5.75 (1H,br t, J=15.5 Hz), 5.67 (1H, d, J=15.5 Hz), 4.42 (2H, s), 4.21 (2H, d, J=4.5 Hz), 3.65-3.80 (4H, m), 3.16 (3H, s), 1.72-1.80 (4H, m); MS (M+H)$^+$=288. Analysis calc'd for C$_{17}$H$_{21}$NO$_3$: C, 71.06; H, 7.37; N, 4.87. Found: C, 70.86; H, 7.14; N, 4.58.

The compounds represented in Table 3 are prepared by alkylation of the appropriate allylic alcohol, obtained as described in Examples 3 or 7 with the requisite 3-heteroaryl-prop-2-yn-yl halide which was prepared as described in the patent literature (EP-385-663, Crawley, G. C.), according to the method of Example 1, step 4.

TABLE 3

Novel Aryl- and Heteroarylacetylene Substituted Olefin Triethers

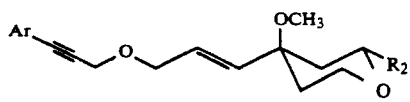

| Example | R$_2$ | Ar |
| --- | --- | --- |
| 23 | H | -2-pyridyl |
| 24 | Me | -2-pyridyl |
| 25 | H | -3-pyridyl |
| 26 | Me | -3-pyridyl |
| 27 | H | -4-pyridyl |
| 28 | Me | -4-pyridyl |
| 29 | H | -2-furyl |
| 30 | Me | -2-furyl |
| 31 | H | -3-furyl |
| 32 | Me | -3-furyl |
| 33 | H | -2-thienyl |
| 34 | Me | -2-thienyl |
| 35 | H | -3-thienyl |
| 36 | Me | -3-thienyl |
| 37 | H | -2-benzo[b]thienyl |
| 38 | Me | -2-benzo[b]thienyl |
| 39 | H | -2-benzo[b]furyl |
| 40 | Me | -2-benzo[b]furyl |
| 41 | H | -2-thiazoyl |
| 42 | Me | -2-thiazoyl |
| 43 | H | -2-imidazoyl |
| 44 | Me | -2-imidazoyl |
| 45 | H | -2-pyrimidyl |
| 46 | Me | -2-pyrimidyl |

We claim:
1. A compound having the structure

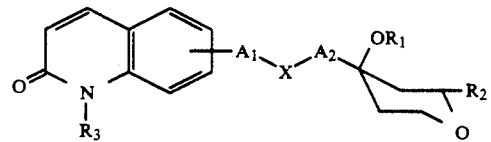

or a pharmaceutically acceptable salt thereof wherein
R$_3$ is hydrogen or alkyl of one to four carbon atoms;
A$_1$ is selected from the group consisting of propynyl, methylene, and a valence bond;
X is selected from the group consisting of oxygen, sulfur, sulfonyl, and NR$_4$, where R$_4$ is hydrogen or alkyl of one to four carbon atoms; and
A$_2$ is selected from the group consisting of

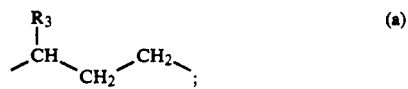

(a)

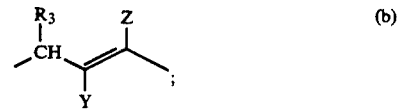

(b)

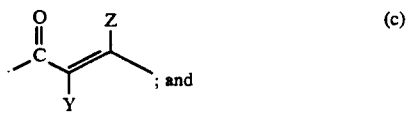

(c)

; and

(d)

wherein $R_3$ is as defined above; Y is hydrogen, halogen, or nitrile, and Z is hydrogen or alkyl of one to four carbon atoms, with the proviso that when X is NH, $A_2$ is

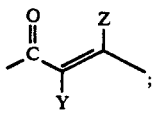

$R_1$ is alkyl of one to four carbon atoms; and
$R_2$ is hydrogen or alkyl of one to four carbon atoms.

2. A compound or pharmaceutically acceptable salt thereof as defined in claim 1 wherein $A_2$ is

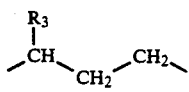

where $R_3$ is defined therein.

3. A compound or pharmaceutrically acceptable salt thereof as defined in claim 1 wherein $A_2$ is

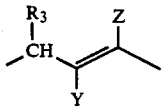

where $R_3$, Y and Z are as defined therein.

4. A compound or pharmaceutically acceptable salt thereof as defined in claim 1 wherein $A_2$ is

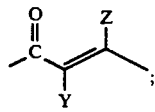

and X is $NR_4$ where X, Y, Z and $R_4$ are as defined therein.

5. A compound or pharmaceutically acceptable salt thereof as defined in claim 1 wherein $A_2$ is

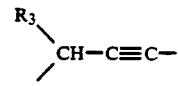

and $R_3$ is as defined therein.

6. A compound or pharmaceutically acceptable salt thereof selected from the group consisting of
4-methoxy-4-(3-((1,2-dihydro-1-methyl-2-oxoquinolin-6-yl)methoxy)-trans-prop-1-enyl)tetrahydropyran,
4-methoxy-4-(3-((1,2-dihydro-1-methyl-2-oxoquinolin-6-yl)methoxy)-trans-prop-1-enyl)-2-methyltetrahydropyran, and
3-(4-methoxytetrahydropyran-4-yl)-N-((1,2-dihydro-1-methyl-2-oxoquinolin-6-yl)methyl)-trans-propionyl amide.

7. A pharmaceutical composition comprising a therapeutically effective amount of a compound as defined by claim 1 in combination with a pharmaceutically acceptable carrier.

8. A method of inhibiting 5-lipoxygenase enzyme activity in a mammal in need of such treatment comprising administering an effective amount of a compound as defined by claim 1.

* * * * *